United States Patent [19]
Flynn

[11] Patent Number: 5,469,842
[45] Date of Patent: Nov. 28, 1995

[54] CPR FACE MASK

[76] Inventor: Stephen Flynn, 255,Chartwell Road, Oakville, Ontario, Canada, L6J 3Z7

[21] Appl. No.: 272,460

[22] Filed: Jul. 11, 1994

[51] Int. Cl.$^6$ .................................................. A61M 16/00
[52] U.S. Cl. ............................. 128/203.11; 128/202.28; 128/202.29
[58] Field of Search ......................... 128/203.11, 202.28, 128/202.29

[56] References Cited

U.S. PATENT DOCUMENTS

| | | | |
|---|---|---|---|
| 3,518,989 | 7/1970 | Seeler | 128/203.11 |
| 3,695,264 | 10/1972 | Laeral | 128/202.28 |
| 4,834,085 | 5/1989 | Webster, II | 128/203.11 |
| 4,886,057 | 12/1989 | Nave | 128/203.11 |
| 5,121,745 | 6/1992 | Israel | 128/203.11 |
| 5,146,914 | 9/1992 | Sturrock | 128/203.11 |
| 5,295,478 | 3/1994 | Baldwin | 128/203.11 |

Primary Examiner—Edgar S. Burr
Assistant Examiner—William J. Deane, Jr.
Attorney, Agent, or Firm—Rogers & Scott

[57] ABSTRACT

A CPR face mask has a substantially toroidal face engaging part positionable on the face of a patient to surround at least the mouth of the patient. A flexible generally conical part having a lower end extending around and is secured to an upper surface of the face engaging part, and an upper end with an aperture through which a CPR giving person can blow air which passes downwardly through the conical part and the toroidal part into the patient's mouth. The flexible generally conical part has a relatively short outwardly extending substantially horizontal portion at the lower end extending around and secured to the upper surface of the face engaging part, a relatively short portion extending upwardly and outwardly from an inner edge of the substantially horizontal portion, a relatively high frusto-conical portion extending upwardly and inwardly from an upper edge of the upwardly and outwardly inclined portion, a relatively short portion extending inwardly and downwardly from an upper edge of the frusto-conical portion and a central cylindrical portion extending upwardly from an inner edge of the inwardly and downwardly extending portion and providing said aperture. The mask can be positioned in a collapsed configuration for storage by downward movement of the central cylindrical portion to cause the frusto-conical portion to fold downwardly and extend into the toroidal face engaging part and can be returned to a ready-to-use configuration by an upward pull on the central cylindrical portion.

3 Claims, 2 Drawing Sheets

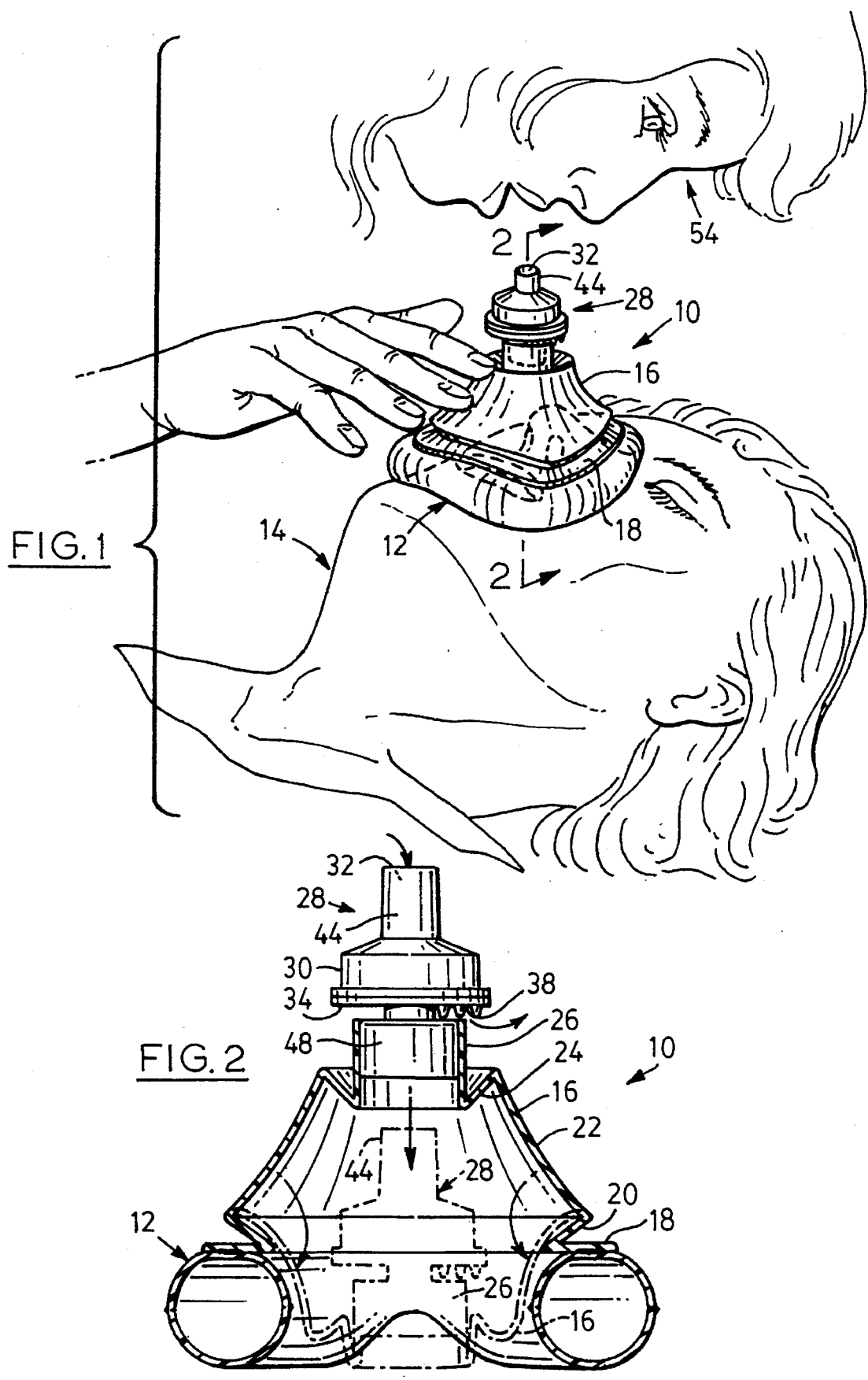

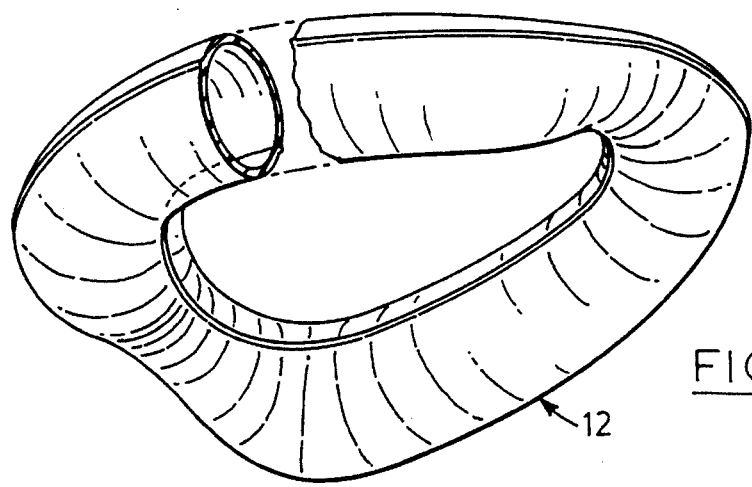
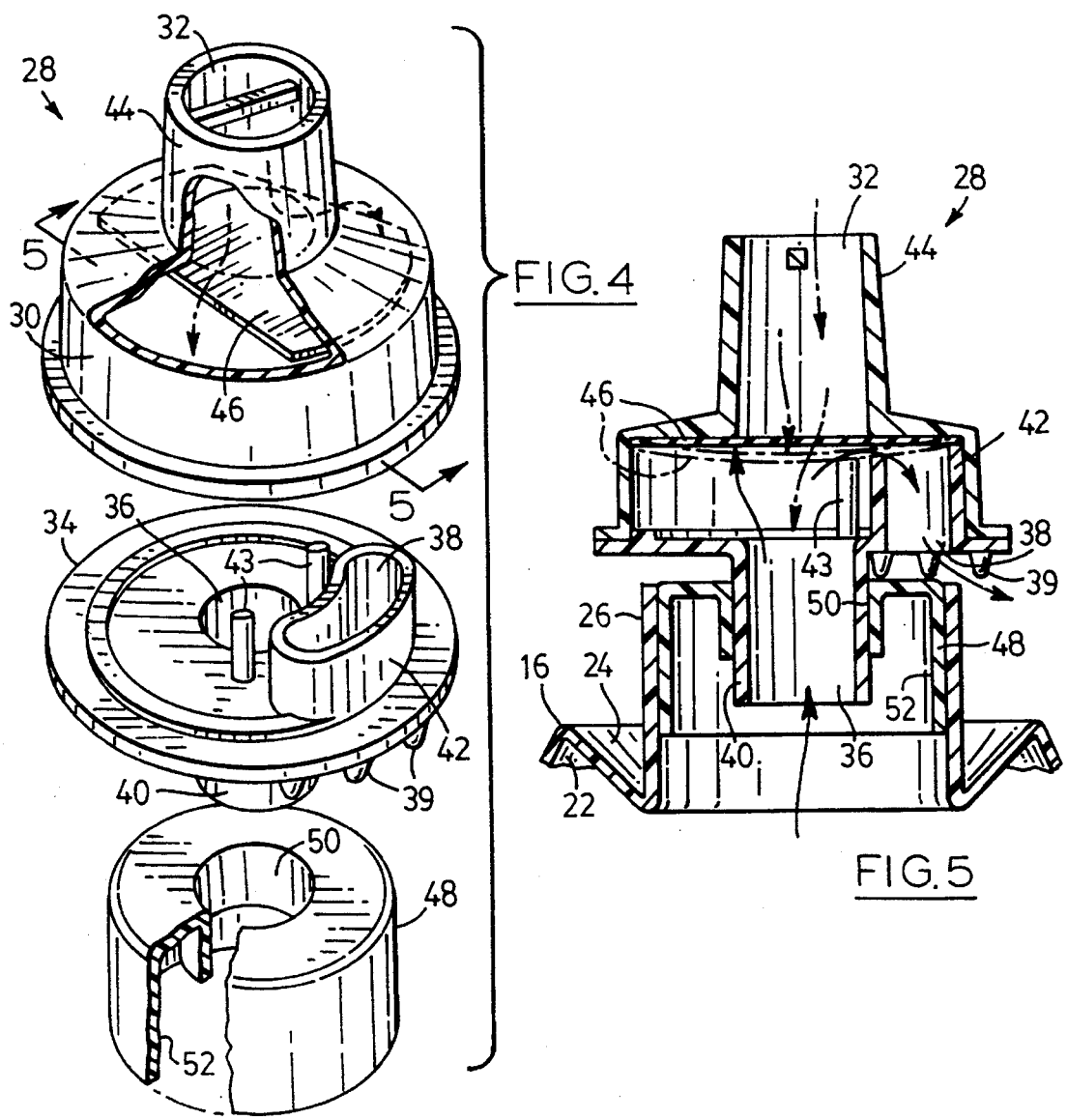

CPR FACE MASK

This invention relates to CPR face masks, namely face masks which are placed over the mouth of a patient requiring cardiopulmonary resuscitation and through which air can be blown into the patient's mouth by a person giving the CPR.

Such face masks are becoming more widely used to avoid the CPR giving person having to be in direct mouth to mouth contact with the patient and hence minimize the risk of infection passing from the patient to the CPR giving person which might occur with direct mouth to mouth contact.

Since such face masks may have to be stored for a considerable period of time before use, they should occupy as small a volume as possible. Collapsible face masks which can be stored in a collapsed condition and can be brought to a ready-to-use condition when needed have been proposed but have not for various reasons proved to be particularly successful in practice.

It is therefore an object of this invention to provide an improved collapsible CPR face mask.

The present invention provides a CPR face mask comprising a substantially toroidal face engaging part positionable on the face of a patient to surround at least the patient's mouth, and a flexible generally conical part having a lower end extending around and secured to an upper surface of the face engaging part, and an upper end with an aperture through which a CPR giving person can blow air which passes downwardly through the conical part and the toroidal part into the patient's mouth. The flexible generally conical part has a relatively short outwardly extending substantially horizontal portion at the lower end extending around and secured to the upper surface of the face engaging part, a relatively short portion extending upwardly and outwardly from an inner edge of the substantially horizontal portion, a relatively high frustoconical portion extending upwardly and inwardly from an upper edge of the upwardly and outwardly inclined portion, a relatively short portion extending inwardly and downwardly from an upper edge of the frustoconical portion and a central cylindrical portion extending upwardly from an inner edge of the inwardly and downwardly extending portion and providing the aperture.

The mask can be positioned in a collapsed configuration for storage by downward movement of the central cylindrical portion to cause the frustoconical portion to fold downwardly and extend into the toroidal face engaging part and can be returned to a ready to use configuration by an upward pull on the central cylindrical portion.

The substantially toroidal face engaging part may be made of flexible material and have a substantially circular hollow cross-section.

The face mask may also include a flow control valve extending upwardly from the central cylindrical portion of the generally conical part, the flow control valve having an upper inlet into which air can be blown by the CPR giving person to pass downwardly through a first outlet and into the face mask and the patient's mouth, the flow control valve causing air passing upwardly from the patient's mouth through the face mask into the first outlet to be released to the external atmosphere through a second outlet without passing to the inlet.

Embodiments of the invention will now be described, by way of example, with reference to the accompanying drawings, of which:

FIG. 1 is a perspective view of a CPR face mask in accordance with the invention being used by a CPR giving person on a patient, FIG. 2 is a sectional view, partly in elevation, along the line 2—2 of FIG. 1, with the collapsed configuration of the face mask being shown in dotted outline, FIG. 3 is a perspective view, partly broken away, of the face engaging part of the face mask, FIG. 4 is an exploded view, partly broken away, of the flow control valve of the face mask, and FIG. 5 is a sectional view of the flow control valve taken along the line 5—5 of FIG. 4.

Referring to the drawings, a CPR face mask 10 has a substantially toroidal face engaging part 12 positionable on the face of a patient 14 to surround the patient's mouth and nose. The toroidal face engaging part 12 is made of flexible plastic material and has a substantially circular hollow cross-section.

The face mask 10 also has a flexible generally conical part 16 also of plastic material and with a relatively short outwardly extending substantially horizontal portion 18 secured by heat sealing to the upper surface of the face engaging part 12. A relatively short portion 20 extends upwardly and outwardly from the inner edge of the substantially horizontal portion 18, and a relatively high frustoconical portion 22 extends upwardly and inwardly from the upper edge of the upwardly and outwardly extending portion 20. A relatively short portion 24 extends inwardly and downwardly from the upper edge of the frusto-conical portion 22, and a central cylindrical portion 26 extends upwardly from the inner edge of the inwardly and downwardly extending portion 24.

The face mask 10 also has a flow control valve 28 extending upwardly from the central cylindrical portion 26 of the downwardly conical part 16. The flow control valve 28 has a two part housing, namely a first housing part 30 which has an inlet 32 and a second housing part 34 which has a first outlet 36 and a second outlet 38. The first outlet 36 is formed by a downwardly extending tubular portion 40 and the second outlet 38 is formed by an upwardly extending tubular portion 42 of short circumferential extent near the periphery of the second housing part 34, the outlet 38 being in communication with the external atmosphere. The inlet 32 is formed by an upwardly extending tubular portion 44. The two housing parts 30, 32 are secured together by a suitable adhesive.

A valve member 46 formed by a sheet of flexible material extends across the interior of the first housing part 30 between the tubular portion 44 and the tubular portion 42.

The flow control valve 28 also includes a tubular adaptor 48 which has an upper opening 50 of relatively small diameter which fits over tubular portion 40 and a lower opening 52 of larger diameter which fits into the central cylindrical portion 26 of the frusto-conical part 16.

The face mask 10 can be positioned in a collapsed condition for storage, as shown in dotted outline in FIG. 2, by downward movement of the central cylindrical portion 26 to cause the frusto-conical portion 22 to fold downwardly and extend into the toroidal face engaging portion 12. As shown, in the collapsed condition, most of the conical portion 16 and the lower part of the flow control valve 28 is located within the toroidal part, thereby producing a compact arrangement for packaging and storage.

In use, the face mask is removed from its package and brought to the ready-to-use configuration by pulling upwardly on the upward extending tubular portion 44 of the flow control valve 28. The CPR giving person 54 then places the face mask 10 on the face of the patient 14 so that the flexible toroidal part 12 engages the face around the mouth and nose of the patient 14.

The CPR giving person 54 then blows into the upwardly extending tubular portion 44 of the flow control valve 28 so that air passes from the CPR giving person's mouth into the flow control valve 28 through the inlet 32. The air pressure causes an end portion of flexible valve member 46 to engage the upper end of tubular portion 42 to block the passageway to the second outlet 38. The second housing part 34 has a pair of posts 43 adjacent to the tubular portion 42 to limit downward movement of the valve member 46. The air blown into flow control valve 28 passes around the sides of valve member 46, as indicated in dotted line in FIGS. 4 and 5, into the downwardly extending tubular portion 40 and through the first outlet 36 and adaptor 48 into the frusto-conical part 16. From the frustoconical part 16, the air passes through the toroidal part 12 into the patient's mouth and nose.

When air is exhaled by the patient 14, the air passes upwardly through the toroidal part 12 and frusto-conical part 16 into the first outlet 36 of the flow control valve 28. However, the passage of the exhaled air moves the valve member 46 upwardly to seal off the tubular portion 44 and opens tubular member 42 and second outlet 38 so that the exhaled air passes to the external atmosphere. The second housing part 34 has a series of external projections 39 surrounding the second outlet 38 to prevent blockage thereof by the adaptor 48.

The advantages of the invention will be readily apparent to a person skilled in the art from the foregoing description of a preferred embodiment. Other embodiments of the invention will also be readily apparent to a person skilled in the art, the scope of the invention being defined in the appended claims.

I claim:

1. A CPR face mask comprising:

a substantially toroidal face engaging part positionable on the face of a patient to surround at least the mouth of the patient, a flexible generally conical part having a lower end extending around and secured to an upper surface of the face engaging part, and an upper end with an aperture through which a CPR giving person can blow air which passes downwardly through the conical part and the toroidal part into the patient's mouth, the flexible generally conical part having a relatively short outwardly extending substantially horizontal portion at the lower end extending around and secured to the upper surface of the face engaging part, a relatively short portion extending upwardly and outwardly from an inner edge of the substantially horizontal portion, a relatively high frusto-conical portion extending upwardly and inwardly from an upper edge of the upwardly and outwardly inclined portion, a relatively short portion extending inwardly and downwardly from an upper edge of the frusto-conical portion and a central cylindrical portion extending upwardly from an inner edge of the inwardly and downwardly extending portion and providing said aperture, whereby the mask can be positioned in a collapsed configuration for storage by downward movement of the central cylindrical portion to cause the frusto-conical portion to fold downwardly and extend into the toroidal face engaging part and can be returned to a ready-to-use configuration by an upward pull on the central cylindrical portion.

2. A CPR face mask according to claim 1 wherein the substantially toroidal face engaging part is made of flexible material and has a substantially circular hollow cross-section.

3. A CPR face mask according to claim 1 also including a flow control valve extending upwardly from the central cylindrical portion of the generally conical part, said flow control valve having an upper inlet into which air can be blown by the CPR giving person and which passes downwardly through a first outlet and through the face mask into the patient's mouth, and said flow control valve causing air passing upwardly from the patient's mouth through the face mask into the first outlet to be released to the external atmosphere through a second outlet without passing to the inlet.

* * * * *